(12) United States Patent
Ariav et al.

(10) Patent No.: US 7,325,460 B2
(45) Date of Patent: Feb. 5, 2008

(54) FORCE SENSOR METHOD AND CONSTRUCTION

(75) Inventors: Arie Ariav, Doar-Na Hof Ashkelon (IL); Vladimir Ravitch, Ashkelon (IL)

(73) Assignee: Nexense Ltd., Yavne (IL)

( * ) Notice: Subject to any disclaimer, the term of this patent is extended or adjusted under 35 U.S.C. 154(b) by 164 days.

(21) Appl. No.: 11/246,271

(22) Filed: Oct. 11, 2005

(65) Prior Publication Data

US 2006/0027028 A1 Feb. 9, 2006

(30) Foreign Application Priority Data

Oct. 10, 2004 (IL) .................................... 164474

(51) Int. Cl.
*G01N 3/08* (2006.01)
(52) U.S. Cl. ............................ 73/820; 73/715; 73/716; 73/717; 73/723
(58) Field of Classification Search ................. 73/715, 73/716, 717, 723, 820
See application file for complete search history.

(56) References Cited

U.S. PATENT DOCUMENTS

| | | | | |
|---|---|---|---|---|
| 5,212,989 | A * | 5/1993 | Kodama et al. ............... | 73/706 |
| 6,621,278 | B2 * | 9/2003 | Ariav ........................... | 324/637 |
| 6,715,356 | B2 * | 4/2004 | Gerst et al. ..................... | 73/715 |
| 6,848,318 | B2 * | 2/2005 | Gerst et al. ..................... | 73/715 |
| 7,021,148 | B2 * | 4/2006 | Kuhn et al. ..................... | 73/715 |
| 2001/0015105 | A1 * | 8/2001 | Gerst et al. ..................... | 73/715 |
| 2002/0105340 | A1 * | 8/2002 | Ariav ........................... | 324/637 |
| 2003/0024319 | A1 * | 2/2003 | Pistorius ....................... | 73/718 |

* cited by examiner

*Primary Examiner*—Edward Leekowitz
*Assistant Examiner*—Freddie Kirkland, III

(57) ABSTRACT

A method of making a force sensor, the force sensor being particularly sensitive the axial component of a force applied along a predetermined axis, of the type including a force-receiving membrane deformable by an applied force to be sensed, the method comprising: providing the force sensor with a body of a liquid, and with a second membrane separated from said force-receiving membrane by the body of liquid; applying the force to be sensed to the center of the force-receiving membrane to thereby pressurize the liquid according to the magnitude and axis of the force applied to the force-receiving membrane; and measuring the deformation of the second membrane; wherein the force-receiving membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of the applied force.

21 Claims, 2 Drawing Sheets

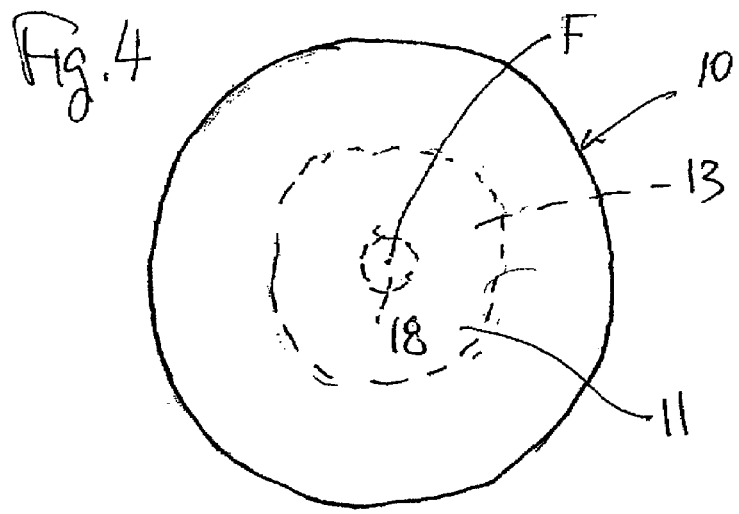
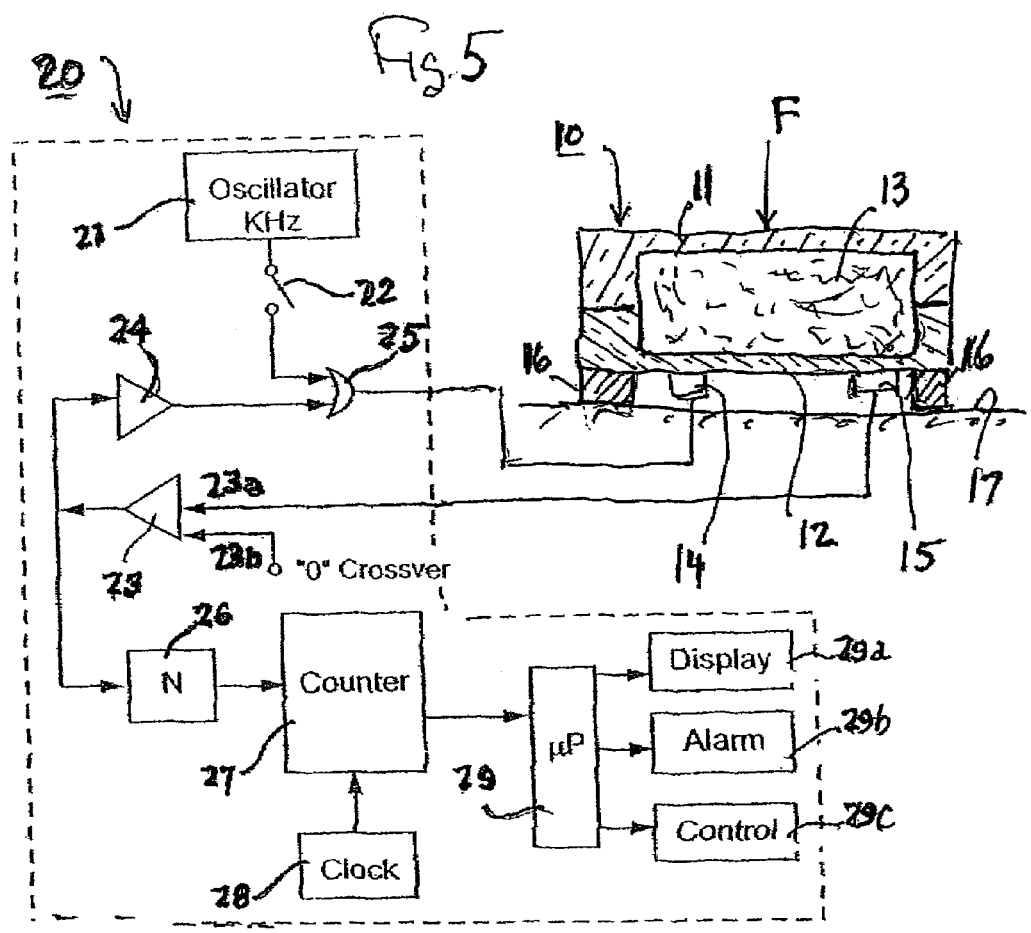

FORCE SENSOR METHOD AND CONSTRUCTION

RELATED APPLICATIONS

The present application claims priority from Israel Patent Application No. 164474, filed on Oct. 10, 2004, the contents of which are incorporated herein by reference.

FIELD AND BACKGROUND OF THE INVENTION

The present invention relates to force sensor methods and constructions. The invention is especially directed to a method of sensing a force in a manner particularly sensitive to the axis at which the force is applied to the sensor, and to force sensors constructed to sense forces in accordance with such method.

A common requirement for force sensors is sensitivity for one axis only; that is, the sensor should be particularly sensitive to forces applied along a predetermined axis. At the present time, various arrangements are used to provide a force sensor with one-axis sensitivity, e.g., special mounting arrangements to assure that the force to be measured is applied only along the predetermined axis, and/or to reduce or eliminate forces applied to the sensor along any other axis. Such arrangements, however, are relatively complicated and/or costly.

OBJECTS AND SUMMARY OF THE PRESENT INVENTION

An object of the present invention is to provide a method of making a force sensor particularly sensitive to forces applied along a predetermined axis. Another object of the invention is to provide a method of sensing a force in a manner particularly sensitive to the axis at which the force is applied to the sensor; and a further object of the invention is to provide a force sensor particularly sensitive to forces applied along a predetermined axis.

According to one aspect of the present invention, there is provided a method of making a force sensor particularly sensitive to the axial component of an applied force, the force sensor being of the type including a force-receiving membrane deformable by an applied force to be sensed, the method comprising: providing the force sensor with a body of a liquid, and with a second membrane separated from the force-receiving membrane by the body of liquid; applying the force to be sensed to the center of the force-receiving membrane to thereby pressurize the liquid according to the magnitude and axis of the force applied to the force-receiving membrane; and measuring the deformation of the second membrane; wherein the force-receiving membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of the applied force.

As will be described more particularly below, providing the force sensor with a body of a liquid between the force-receiving membrane and the second membrane, and measuring the deformation of the second membrane, makes the force sensor particularly sensitive to forces applied along a predetermined axis, namely the axis perpendicular to the plane of the force-receiving membrane. As will be described more particularly below, the liquid between the two membranes would thus be pressurized not only according to the magnitude of the applied force, but also according to the axis at which the force is applied.

Actually, measuring the deformation of the second membrane merely produces a measurement of the pressure of the liquid between the two membranes. Therefore, the invention could also be implemented in a force sensor in which the second membrane is not provided, but rather the pressurization of the liquid is measured in a different manner, e.g., by a conventional pressure sensor.

According to another aspect of the present invention, therefore, there is provided, a method of sensing the axial component of a force by means of a sensor of the type including a deformable membrane, the method comprising: providing the sensor with a chamber which is filled with a liquid and which is closed at one side by the deformable membrane; applying the force to be sensed to the central region of the deformable membrane, to thereby pressurize the liquid according to the magnitude of the axial component of the force applied to the deformable membrane; and measuring the pressure of the liquid in the chamber; wherein the deformable membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of the applied force.

The pressure of the liquid in the chamber may be measured by a conventional liquid pressure sensor, as indicated above. However, in the preferred embodiment of the invention described below the pressure of the liquid in the chamber is measured by closing another side of the chamber with a second deformable membrane, and measuring the deformation of the second membrane.

Particularly good results are obtainable when the deformation of the second membrane is measured according to the technique described in U.S. Pat. No. 6,621,278 and International Patent Application PCT/IL04/000138, filed on Feb. 12, 2004, the contents of which are incorporated herein by reference. According to the technique described in that Patent and International Application, the deformation of the second membrane is measured by:

a) transmitting a cyclically-repeating energy wave through a transmission channel in, or carried by, the second membrane;

b) changing the frequency of the transmission while maintaining the number of waves in a loop including the transmission channel as a whole integer; and c) utilizing the changes in frequency of the transmission to provide an indication of the deformation of the second membrane, and thereby of the force applied to the first membrane along the predetermined axis.

According to further features in the described preferred embodiment, the cyclically-repeating energy wave is an acoustical wave; and the transmission channel is of an elastomeric material having high transmissivity and low attenuation properties with respect to the cyclically-repeating energy wave.

According to a still further aspect of the present invention, there is provided a force sensor particularly sensitive to the axial component of an applied force, comprising: a housing having a chamber filled with a liquid; a deformable membrane closing one side of the chamber such that the inner surface of the membrane contacts the liquid, and the outer surface of the membrane is adapted to receive at its center region the force to be sensed, to thereby pressurize the liquid according to the magnitude and axis of the force applied to the central region of the membrane; and means for measuring the pressure of the liquid in the chamber; wherein the deformable membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of the applied force.

According to further features in the described preferred embodiment, the means for measuring the pressure of the liquid in the chamber includes: a second deformable membrane closing another side of the chamber; and a deformation measuring system for measuring the deformation of the second deformable membrane.

As indicated above, the deformation measuring system preferably, comprises:

a) a transmitter for transmitting a cyclically-repeating energy wave through a transmission channel in, or carried by, the second deformable membrane;

b) a receiver for receiving the cyclically-repeating energy wave transmitted through the transmission channel; and c) a processor for changing the frequency of transmission of the cyclically-repeating energy wave through the transmission channel while maintaining the number of waves in a loop including the t transmission channel as a whole integer, and for utilizing the changes in frequency to produce a measurement of the deformation of the second deformable membrane.

As will be described more particularly below, the foregoing features of the present invention enable relatively simple, inexpensive, and efficient force sensors to be constructed which are particularly sensitive to forces applied along a predetermined axis.

Further features and advantages of the invention will be apparent from the description below.

BRIEF DESCRIPTION OF THE DRAWINGS

The invention is herein described, by way of example only, with reference to the accompanying drawings, wherein:

FIG. 4 is a plan view of the force sensor of FIG. 1; and

FIG. 5 is a block diagram illustrating a preferred form of control and processing circuit used with the force sensor of FIG. 1.

It is to be understood that the foregoing drawings, and the description below, are provided primarily for purposes of facilitating understanding the conceptual aspects of the invention and various possible embodiments thereof, including what is presently considered to be a preferred embodiment. In the interest of clarity and brevity, no attempt is made to provide more details than necessary to enable one skilled in the art, using routine skill and design, to understand and practice the described invention. It is to be further understood that the embodiments described are for purposes of example only, and that the invention is capable of being embodied in other forms and applications than described herein.

DESCRIPTION OF A PREFERRED EMBODIMENT

Figure 1:
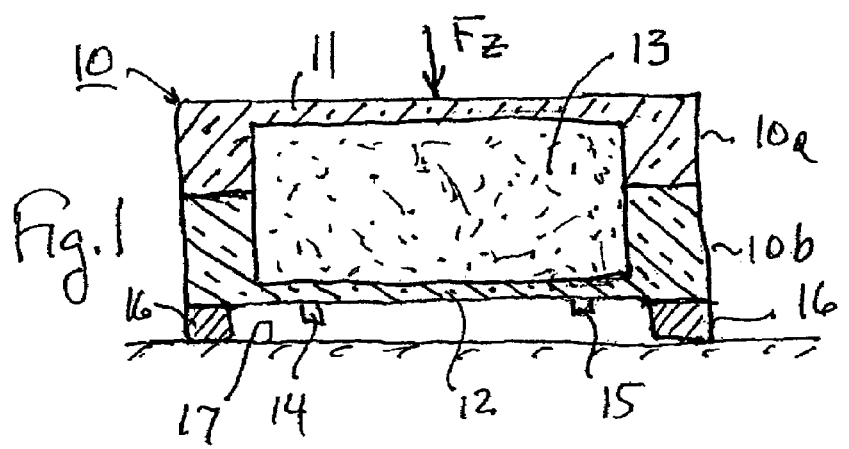
FIG. 1 is a sectional view illustrating one form of force sensor constructed in accordance with the present invention.

FIG. 1 is a sectional view illustrating a force sensor constructed in accordance with the present invention so as to be particularly sensitive to forces applied along a predetermined axis, namely axis $F_Z$. Such a sensor includes a housing, generally designated 10, closed at one side by a first deformable membrane 11, and on the opposite side by a second deformable membrane 12. Housing 10, with the two deformable membranes 11, 12 on its opposite sides, define a chamber 13 filled with a liquid, which chamber is closed on one side by deformable membrane 11, and on the opposite side by deformable membrane 12. Thus, the inner surfaces of the two membranes contact the liquid within chamber 13. The outer surface of membrane 11 is adapted to receive, at its center region, the force to be sensed, indicated by arrow $F_Z$. It will thus be seen that the application of force $F_Z$ to the center region of membrane 11 will pressurize the liquid within chamber 13 according to the magnitude and axis of the force $F_Z$.

Figure 2:
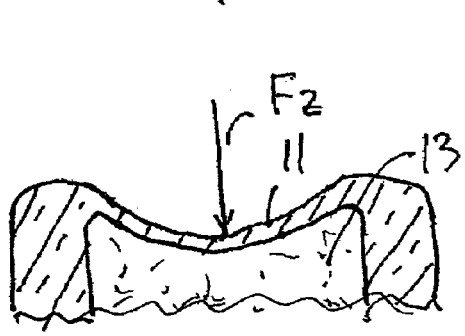
FIGS. 2 and 3 are diagrams helpful in explaining the manner by which the force sensor illustrated in FIG. 1 is particularly sensitive to forces applied along a predetermined axis.

Thus, as shown in FIG. 1, membrane 11 is of a non-undulating configuration in its normal condition. As seen in FIG. 2, if the force $F_z$ is applied to the center region of membrane 11 substantially perpendicularly to the plane of membrane 11 in its initial state, the central region of membrane 11 will be displaced inwardly according to the magnitude of the applied force, to assume the uniform, bowed shaped or concave configuration illustrated in FIG. 2. Such a deformation of membrane 11 will maximize the pressure applied to the liquid 13 within chamber 11 for the respective force applied.

Figure 3:
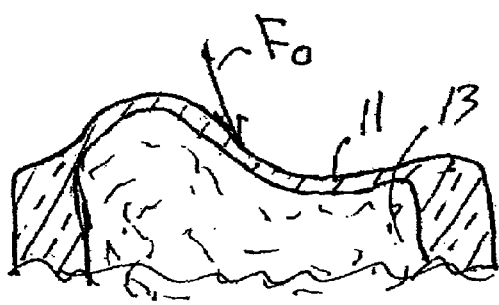

However, as can be seen from FIG. 3, if the force to be sensed is applied obliquely to the central region of membrane 11 (as shown by force $F_O$ in FIG. 3), the membrane will not be displaced uniformly to assume the bowed shape of FIG. 2, but rather will be displaced to assume the undulating shape illustrated in FIG. 3. This is because the pressure applied to the liquid within chamber 13, being uniformly directed in all directions by the liquid, will tend to deform the membrane inwardly in the direction of the applied force to produce the inwardly bowed section 11a, but the pressurized liquid will tend to deform the other side of the membrane to produce the outwardly bulged section 11b.

Accordingly, whereas an axially-applied force $F_Z$ to the membrane 11 will produce a uniform concave deformation of the membrane to maximize the pressurization of the liquid within liquid chamber 13 as shown in FIG. 2, an obliquely-applied force, as shown at $F_O$ in FIG. 3 will produce an undulating-type deformation of the membrane, resulting in a substantially less pressurization of the liquid within chamber 13, according to axial component of the applied force, as will be shown below.

The liquid within chamber 13 is preferably an oil, but it will be appreciated that other liquids could be used for this purpose.

It will thus be seen that the pressure of the liquid within chamber 13, resulting from the deformation of membrane 11 by the force applied to the central region of that membrane, will be dependent not only on the magnitude of the applied force, but also the axis along which the force is applied with respect to the membrane.

Thus, when the axis of the applied force deviates from perpendicularity, the pressure decreases according to the Cosine Function of the deviation angle. That is, any obliquely-applied force ($F_O$) has two components:

$F_Z = f * \text{Cos(deviation angle)}$, and $F_Y = F * \text{Sin(deviation angle)}$.

In the case of an ideal sensor having sensitivity only for the Z-axis, its sensitivity will therefore correspond to the cosine of the deviation.

The pressure of the liquid within chamber 13 may be measured in any convenient manner. For example, conventional pressure sensors can be used for measuring the pressure of the liquid. Particularly, good results are obtainable, however, when this pressure is measured by using the second deformable membrane 12, and by measuring its deformation in accordance with the technique described in the above-cited U.S. Pat. No. 6,621,278 and International Patent Application PCT/IL04/000138.

As will be described more particularly below with respect to FIG. 5, when using this technique for measuring the pressure of the liquid within chamber 13, the second deformable membrane 12, closing the other side of chamber 13, is provided with: a transmitter 14 on its outer surface for transmitting a cyclically-repeating energy wave through a transmission channel in, or carried by, membrane 12; and a receiver 15 for receiving the cyclically-repeating energy wave transmitted through the transmission channel. The apparatus further includes a processor (described below with respect to FIG. 5) for changing the frequency of transmission of the cyclically-repeating energy wave through the transmission channel while maintaining the number of waves in the loop including the transmission channel as a whole integer. The processor utilizes the changes in frequency to produce a measurement of the deformation of membrane 12.

In the preferred embodiment of force sensor illustrated in FIGS. 1 and 4, the two deformable membranes 11, 12 are integrally formed with the housing 10. For this purpose, housing 10 may be made of two sections, shown at 10a, 10b, each formed with a central recess to define: a relatively thin membrane in one section 10a, to serve as deformable membrane 11; a relatively thin membrane in the other section 10b, to serve as deformable membrane 12; and a cavity between the two sections, to serve as chamber 13 to be filled with the liquid between, and in contact, with the two deformable membranes. Preferably, housing section 10b carrying the transmitter 14 and receiver 15, is formed with a spacer 16 engageable with a supporting or mounting surface 17 to space the transmitter and receiver therefrom, and thereby to permit deformation of membrane 12 in accordance with the forces applied to membrane 11.

It will thus be seen that, in such a construction, membrane 12 defines the transmission channel through which the cyclically-repeating energy wave is transmitted by transmitter 14 and received by receiver 15. It will be appreciated, however, that the transmission channel carrying the transmitter 14 and receive 15 could be a separate member fixed to membrane 12, for example as described in the above-cited International Patent Application PCT/IL04/000138. In either case, the transmission channel between transmitter 14 and receiver 15 is preferably of an elastomeric material having high transmissivity and low attenuation properties with respect to the cyclically-repeating energy wave, as also described in the above-cited International Patent Application PCT/IL04/000138.

In the example illustrated in FIGS. 1 and 4, housing 10 of the force sensor, and also its two deformable membranes 11, 12, as well as its liquid chamber 13, are all of a circular configuration. It will be appreciated, however, that the housing and/or membranes could be of other configurations. Preferably, the force receiving membrane 11 should be symmetrical about its central area, shown at 18 in FIG. 4, so that the membrane will be uniformly displaceable about its central region when an axial force is applied thereto, as described above with respect to FIG. 2.

FIG. 5 more particularly illustrates a preferred circuit, generally designated 20, according to the above-cited U.S. Pat. No. 6,621,278 and International Patent Application PCT/IL04/000138, which may be used with the force sensor of FIGS. 1 and 4 to produce a very precise measurement of the pressurization of the liquid within chamber 13, and thereby a measurement of the force applied to membrane 11, i.e., to the central region 18 of that membrane along the axis $F_Z$. Briefly, such a system operates by: (a) transmitting from transmitter 14 a cyclically-repeating energy wave through the transmission channel defined by membrane 12 with receiver 15; (b) changing the frequency of the transmission while maintaining the number of waves in the loop including the transmission channel as a whole integer; and (c) utilizing the changes in frequency of the transmission to provide an indication of the deformation of membrane 12, and thereby of the force applied to membrane 11.

In the described preferred embodiment, the cyclically-repeating energy wave is an acoustical wave. In addition, operation (b) includes: detecting a predetermined fiducial point in each cyclically-repeating energy wave received by receiver 15; and continuously changing the frequency of the transmission in accordance with the detected fiducial point of each received energy wave such that the number of energy waves in the loop of the transmission channel is a whole integer.

More particularly, the system illustrated in FIG. 5 operates as follows: Initially, oscillator 21 is energized while switch 22 is closed so as to cause transmitter 14 to transmit a succession of sonic pulses until such pulses are received by receiver 15. Once the pulses are received by receiver 15, switch 22 is opened so that the pulses received by receiver 15 are thereafter used for controlling the transmitter 14.

As shown in FIG. 5, the sonic signals received by receiver 15 are fed to a comparator 23 via its input 23a. Comparator 23 includes a second input 23b connected to a predetermined bias so as to detect a predetermined fiducial or reference point in the received signal. In the example illustrated in FIG. 5, this predetermined fiducial point is the "zero" cross-over point of the received signal; therefore, input 23b of comparator 23 is at a zero bias.

The output of comparator 23 is fed to an amplifier 24, e.g., a monostable oscillator, which is triggered to produce an output signal at each fiducial point (zero cross-over point) in the signals received by receiver 15. The outputs from amplifier 24 are fed via an OR-gate 25 to trigger the transmitter 14 for the next sonic pulse. Since switch 22 is open, transmitter 14 will thus be triggered by each signal received by the receiver 15 to transmit the next sonic pulse in the succession of pulses.

It will thus be seen that the frequency of the output pulses or signals from transmitter 15 will change with a change in the spacing between the transmitter 14 and receiver 15. It will also be seen that the number of wavelengths or pulses in the loop including transmitter 14 and receiver 15 will be a whole integer. This change in frequency by the transmitter 14, while maintaining the number of waves between the transmitter and receiver 15 as a whole integer, enables a precise determination to be made of the distance between the transmitter and receiver, and thereby of the deformation of membrane 11.

A summing circuit, including counter 26, counter 27, clock 28 and microprocessor 29, enables the detected frequency difference, and thereby the measurement precision, to be increased by a factor "N". Thus, the precision of the measurement can be preset, almost without limitation, by the selection of the appropriate frequency, clock rate for clock 28, and summation factor "N" for counter 27.

As further shown in FIG. 5, the output from microprocessor 29 of the control and processor circuit 20 may be used for display, alarm and/or control purposes, as schematically shown at 29a, 29b and 29c.

Further details of the construction and operation of such a measuring circuit is described in the above-cited U.S. Pat. No. 6,621,278 and International Patent Application PCT/IL04/000138.

It will be appreciated that the invention has been described with respect to one preferred embodiment for purposes of example only, and that many variations, modifications and other applications of the invention may be made. For example, other means, such as conventional pressure sensors, may be used for measuring the pressure of the liquid within chamber 13. In addition, other means, such as strain gauges, may be used for measuring the deformation of membrane 12. Further, the invention could be implemented with other housing structures, for example housing structures wherein one or both of the membranes are not integrally formed with the housing, but rather are separate elements mounted to the housing by conventional mounting structures. Also, other housing configurations could be used according to the particular application.

Many other variations, modifications and applications of the invention will be apparent.

What is claimed is:

1. A method of making a force sensor, particularly sensitive to the axial component of an applied force, said force sensor being of the type including a force-receiving membrane deformable by an applied force to be sensed, said method comprising:
    providing the force sensor with a body of a liquid, and with a second membrane separated from said force-receiving membrane by said body of liquid;
    applying the force to be sensed to the center of said force-receiving membrane to thereby pressurize said liquid according to the magnitude and axis of the force applied to said force-receiving membrane; and
    measuring the deformation of said second membrane;
    wherein said force-receiving membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of said applied force.

2. The method according to claim 1, wherein the deformation of said second membrane is measured by:
    (a) transmitting a cyclically-repeating energy wave through a transmission channel in, or carried by, said second membrane;
    (b) changing the frequency of the transmission while maintaining the number of waves in a loop including said transmission channel as a whole integer; and
    (c) utilizing the changes in frequency of the transmission to provide an indication of the deformation of said second membrane, and thereby of the force applied to said first membrane along said predetermined axis.

3. The method according to claim 2, wherein operation (b) includes:
    detecting a predetermined fiducial point in each cyclically-repeating energy wave by said receiver; and
    changing the frequency of said transmission in accordance with the detected fiducial point of each received energy wave such that the number of energy waves in the loop of said transmission channel is a whole integer.

4. The method according to claim 2, wherein said cyclically-repeating energy wave is an acoustical wave.

5. The method according to claim 2, wherein said transmission channel is of an elastomeric material having high transmissivity and low attenuation properties with respect to said cyclically-repeating energy wave.

6. A method of sensing the axial component of a force by means of a sensor of the type including a deformable membrane, said method comprising:
    providing the sensor with a chamber which is filled with a liquid and which is closed at one side by said deformable membrane;
    wherein said deformable membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of said applied force;
    applying the force to be sensed to the central region of said deformable membrane, to thereby pressurize said liquid according to the magnitude of the axial component of the force applied to said deformable membrane; and
    measuring the pressure of the liquid in said chamber.

7. The method according to claim 6, wherein the pressure of the liquid in said chamber is measured by closing another side of said chamber with a second deformable membrane, and measuring the deformation of said second membrane.

8. The method according to claim 7, wherein the deformation of said second membrane is measured by:
    (a) transmitting a cyclically-repeating energy wave through a transmission channel in, or carried by, said second membrane;
    (b) changing the frequency of the transmission while maintaining the number of waves in a loop including said transmission channel as a whole integer; and
    (c) utilizing the changes in frequency of the transmission to provide an indication of the deformation of said second membrane, and thereby of the force applied to said first membrane along said predetermined axis.

9. The method according to claim 8, wherein said cyclically-repeating energy wave is an acoustical wave.

10. The method according to claim 8, wherein said transmission channel is of an elastomeric material having high transmissivity and low attenuation properties with respect to said cyclically-repeating energy wave.

11. The method according to claim 6, wherein said second membrane is of circular configuration.

12. A force sensor particularly sensitive to the axial component of an applied force, comprising:
    a housing having a chamber filled with a liquid;

a deformable membrane closing one side of said chamber such that the inner surface of the membrane contacts said liquid, and the outer surface of said membrane is adapted to receive at its center region the force to be sensed, to thereby pressurize said liquid according to the magnitude and axis of the force applied to said central region of the membrane; and means for measuring the pressure of the liquid in said chamber;

wherein said deformable membrane is of a non-undulating configuration in its normal condition and is deformable, by a force applied to its center at an oblique angle to its surface, into an undulating configuration, to include an inwardly-bowed section on one side of its center, and an outwardly-bulged section on the opposite side of its center, such that the liquid body is pressurized by the applied force only according to the axial component of said applied force.

13. The force sensor according to claim 12, wherein said means for measuring the pressure of the liquid in said chamber includes:

a second deformable membrane closing another side of said chamber; and a deformation measuring system for measuring the deformation of said second deformable membrane.

14. The force sensor according to claim 13, wherein said housing includes a spacer member externally of the housing for spacing said second deformable membrane from an external supporting surface to accommodate deformation of said second deformable membrane.

15. The force sensor according to claim 13, wherein said deformable membranes are of circular configuration.

16. The force sensor according to claim 13, wherein said deformable membranes are integrally formed in said housing.

17. The force sensor according to claim 13, wherein said deformation measuring system comprises:

(a) a transmitter for transmitting a cyclically-repeating energy wave through a transmission channel in, or carried by, said second deformable membrane;

(b) a receiver for receiving said cyclically-repeating energy wave transmitted through said transmission channel; and (c) a processor for changing the frequency of transmission of the cyclically-repeating energy wave through said transmission channel while maintaining the number of waves in a loop including said t transmission channel as a whole integer, and for utilizing the changes in frequency to produce a measurement of said deformation of the second deformable membrane.

18. The force sensor according to claim 17, wherein said cyclically-repeating energy wave is an acoustical wave.

19. The force sensor according to claim 17, wherein said transmission channel is of an elastomeric material having high transmissivity and low attenuation properties with respect to said cyclically-repeating energy wave.

20. The force sensor according to claim 17, wherein said processor detects a predetermined fiducial point in each wave received by said receiver and utilizes the detected fiducial point of each received wave to trigger the transmitter such that the number of waves in the loop of said transmission channel is a whole integer.

21. The apparatus according to claim 12, wherein the liquid within said chamber is an oil.

* * * * *